United States Patent [19]

Hintz

[11] Patent Number: 4,635,182
[45] Date of Patent: Jan. 6, 1987

[54] APPARATUS FOR CONTROLLING MULTIPLE TIME-VARYING PROCESSES

[75] Inventor: Kenneth J. Hintz, Fredericksburg, Va.

[73] Assignee: The United States of America as represented by the Secretary of the Navy, Washington, D.C.

[21] Appl. No.: 627,707

[22] Filed: Jul. 3, 1984

[51] Int. Cl.[4] .................. G06F 15/46; G05B 13/02
[52] U.S. Cl. ................... 364/138; 364/148; 364/153; 364/165; 364/179; 364/557
[58] Field of Search ........... 364/138, 139, 148, 152, 364/153, 154, 164, 165, 178, 179, 550, 551, 505, 506, 557

[56] References Cited

U.S. PATENT DOCUMENTS

| | | | |
|---|---|---|---|
| 3,557,349 | 1/1971 | Griem, Jr. | 364/138 X |
| 3,824,387 | 7/1974 | Garst | 364/179 |
| 3,826,903 | 7/1974 | Varasso | 364/138 |
| 3,912,912 | 10/1975 | Pollock | 364/138 |
| 4,161,782 | 7/1979 | McCracken | 364/179 X |

Primary Examiner—Joseph Ruggiero
Attorney, Agent, or Firm—Kenneth E. Walden; Frederick A. Wein; John G. Wynn

[57] ABSTRACT

An apparatus for and a method of controlling multiple time varying processes by a central control device through a use of an adaptive data acquisition scheme is disclosed. A state estimator is used to extrapolate the current state of each control process as well as an estimate of the uncertainty of each state estimate. The state whose uncertainty is greatest is selected. The selected process is then measured, estimated, and a control variable calculated. Use of this selection criteria allows a single control device to effectively control more time varying processes then if the controls had been determined by a controller using a fixed sampling rate. Statistics for each process are updated with each measurement in order to compensate for the time/varying nature of the processes.

5 Claims, 3 Drawing Figures

APPARATUS FOR CONTROLLING MULTIPLE TIME-VARYING PROCESSES

BACKGROUND OF THE INVENTION

1. Field of the Invention

The present invention relates to an apparatus for and a method of controlling multiple time-varying processes through the use of an adaptive data acquisition scheme, but more specifically, it relates to an adaptive control device wherein a state estimator is used to extrapolate the current state of each controlled process as well as an estimate of the uncertainty of each state.

2. Description of the Prior Art

A process is a "specific, continuous action, operation, of series of changes." More specifically, a process may be the mixing of chemicals to form a compound, the refining of crude oil into its constituents, the movement of a mechanical device, or the maneuvering of a target being tracked by radar, among others. The control of state of each one of the foregoing processes is usually done by a dedicated controller. Many of the processes proceed at rates which are slow relative to the processing capabilities of digital computers which can be used for control. Also, processes may proceed at variable rates which require more detailed attention at some times than at others to ensure the same quality of control.

An alternative to the use of a dedicated controller for each process is to use a centralized controller with distributed control or estimation of the various processes. If the processes are deterministic, well understood, and proceed at constant rates, then the sequencing of measurements of each process for state estimation and control is straightforward. However, if the dynamics of the process, the statistics associated with the noise in the process or noise in the measurements are time variant, other methods of determining the sequence of data acquisition must be employed to ensure adequate and stable control.

Prior art methods of centralized control, as far as is known, are based on fixed sampling rates. These sampling rates are determined by the dynamics of the process, the noise associated with the measurements of the process and the magnitude of the uncertainties about the processes to be controlled. For a given set of conditions, a sampling rate can be chosen which will insure a stable control system. However, if the dynamics or statistic of a process change, the sampling rate may be insufficient or too high. In the first case, this leads to system instability and in the latter case a waste of computer time.

It has been shown in a theoretical study of sequence methods for data acquisition, ("Information Directed Data Acquisition", K. J. Hintz, Doctoral Dissertation, University of Virginia, August 1980), that various criteria can be used for selecting which of several processes to update when multiple processes are to be controlled by a single central processor. Although a specific example of the use for a device implementing these theoretical concepts was presented (ibid., page 2), no specific implementation information was presented. Consequently, there is a need in the prior art to configure a specific implementation of the conceptual ideas presented in the reference document so as to configure an adaptive control device for controlling time varying processes in an improved manner.

An example of the use of the foregoing method might be in the operation of a heat/cool system. The central controller device used in such a system would have many functions to perform but they need not all be performed simultaneously. The central control element can apportion its time dynamically to the various tasks under its control based on their need for central processor interaction. This central processor may control the actions of several distributed processors each assigned a particular task. The amount of time or effort the central processor applies to monitoring each task is based on its uncertainty about the state of that task. It can also be decided how much of its efforts can be devoted to assisting that distributed processor in doing its task.

The prior art, as indicated hereinabove, included advances in adaptive control of processes, including control of time varying processes. However, in so far as can be determined, no prior art adaptive control processing device incorporates all of the features and advantages of the present invention.

OBJECTS OF THE INVENTION

Accordingly, a principal object of the present invention is to configure an apparatus which adapts to the changing environment and dynamics of a plurality of processes under its control so as to insure an adequate level of control.

Another object of the present invention is to effectively control widely dispersed and time varying processes using a central control device in an improved manner.

A further object of the present invention is to effectively apportion the processing time of a central control device among several distributed control elements which require the increased computing capability of a more sophisticated device.

Yet another object of the present invention is to more effectively use a central control device by controlling more processes in an improved manner.

SUMMARY OF THE INVENTION

In accordance with the above stated objects, other objects, features and advantages, the purpose of the method and apparatus according to the present invention is to efficiently and effectively use data acquisition or computational capability when the states of multiple processes are to be estimated.

The essence of the present invention is in the use of an apparatus configured such that the technique for controlling data acquisition for estimation of the state of multiple processes is based on a maximal information criteria. The disclosed apparatus adapts to the changing conditions and statistics of the process, adaptively allocating data acquisition resources as several processes proceed. In spite of long term variations of process and measurement statistics, the apparatus provides the instanteous best choice of which process to acquire data from.

The purpose of the present invention is carried out by configuring an adaptive control apparatus to include an electronic data selector which gathers data at its input from a plurality of processes to be controlled, a temperature estimator (for example a digital implementation of a Kalman filter tailored to the processes to be controlled). A data sequencer for comparing the values of the uncertainties in each state estimate and selected the number of the process with the greatest uncertainty, a digital substractor for computing the error between a reference input and the state estimate, a digital multiplier for multiplying the output of the digital substractor by a fixed constant so as to scale a control signal to the proper value, and an electronic data distributor which is operatively connected to the aforementioned data sequencer and the digital multiplier and at its output to each of the aforementioned processes to be controlled. The electronic data distributer passes the control signal on its input to any one of the aforementioned processes to be controlled based on the value of the selected signal from the data sequencer.

BRIEF DESCRIPTION OF THE DRAWINGS

The previously stated objects, and other objects, features and advantages of the present invention will be apparent from the following more particular description of a preferred embodiment as illustrated in the accompanying drawings, in which.

DESCRIPTION OF THE PREFERRED EMBODIMENT

Figure 1:
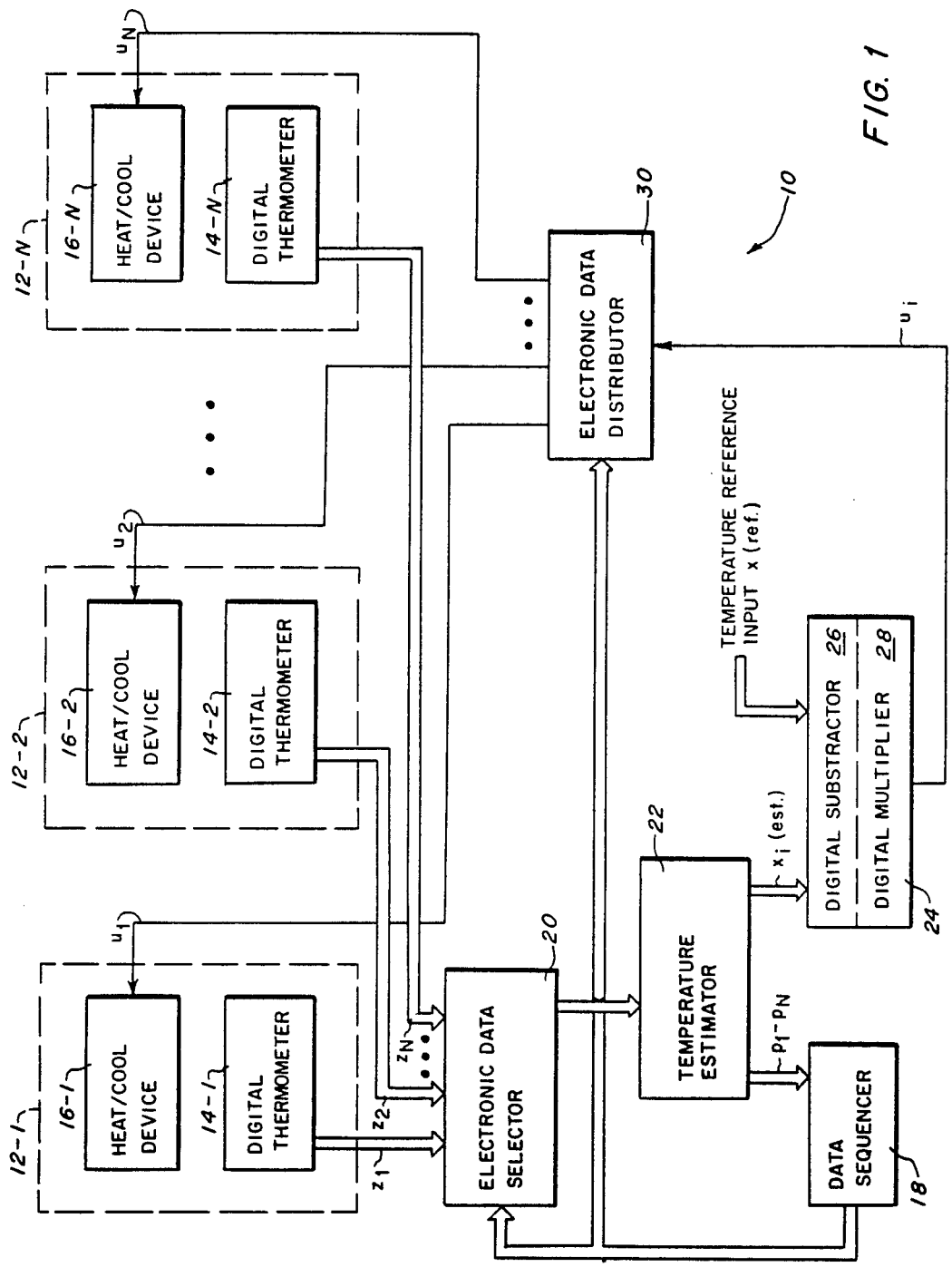
FIG. 1 is a block diagram representation of an adaptive control apparatus according to the present invention depicting, inter alia, the adaptive control of a plurality of heat/cool processes, and the data sequencer and temperature estimator used for control thereof.

FIG. 1 shows an embodiment of an adaptive control apparatus in which the present invention is employed to control multiple time varying processes wherein the method of controlling the data acquisition for estimation of the state of multiple processes is based on a maximal information criteria. A plurality of processes to be controlled 12-1 through 12-N are operatively connected to the adaptive control apparatus 10. In the example shown, a room in a building is subjected to a variety of uncontrollable influences which are referred to as "process noise". This is a "non-stationary, time-varying process" whose statistics change with time. Each of the aforementioned processes includes at its particular location a plurality of digital thermometers 14-1 through 14-N corresponding to the aforementioned processes 12-1 through 12-N. Also included are a corresponding plurality of heat/cool devices 16-1 through 16-N. Measurements $z_1$, $z_2$ through $z_N$ from each digital thermometer 14-1, 14-2 through 14-N, respectively, are fed to an electronic data selecter 20 which responds to a select control signal from a data sequencer 18 and routes selected data ($z_i$) through to a temperature estimator 22. For purposes of the present invention, the temperature estimator 22 is a digital implementation (realization) of a Kalman filter tailored to the processes to be controlled. The temperature estimater 22 takes measurements of the temperature ($z_i$) and combines them with a mathematical model of the process under control along with internally computed estimates of the statistics of the measurements and process noise to produce an estimate of the temperature of the selected process. Kalman filter theory is well known in the prior art.

Continuing, the adaptive control apparatus 10 further comprises a control device 24 which includes a digital substractor 26 and a digital multiplier 28. The control device 24 computes the difference in the reference input x(ref) and the state estimate input $x_i$(est) and computes a control signal proportional to the error between the two. The control signal drives an electronic data distributer 30, which in turn, controls at its output the aforementioned plurality of heat/control devices 16-1, 16-2 through 16-N.

The data sequencer 18 which also is operatively connected to the electronic data selector 20 compares the values of the uncertainties $p_1$ through $p_N$ in each state estimate and selects the number of the process 12-1 through 12-N with the greatest uncertainty. This digital number is then used to set the electronic data selecter 20 and the electronic data distributer 30 to close the control loop for that particular process.

The digital substractor 26 of the control device 24 is configured to compute the error between the reference input x(ref) and the state estimate input $x_i$(est). The digital multiplier 28 of the aforementioned control device 24 is configured to multiply the output of the digital substractor 26 by a fixed constant to scale the control signal to the proper value ($u_i$) The electronic data distributer 30 therefore is configured to electronically pass the control signal on its input to any one of its outputs based on the value of the selecter control signal.

STATEMENT OF THE OPERATION

Figure 2:
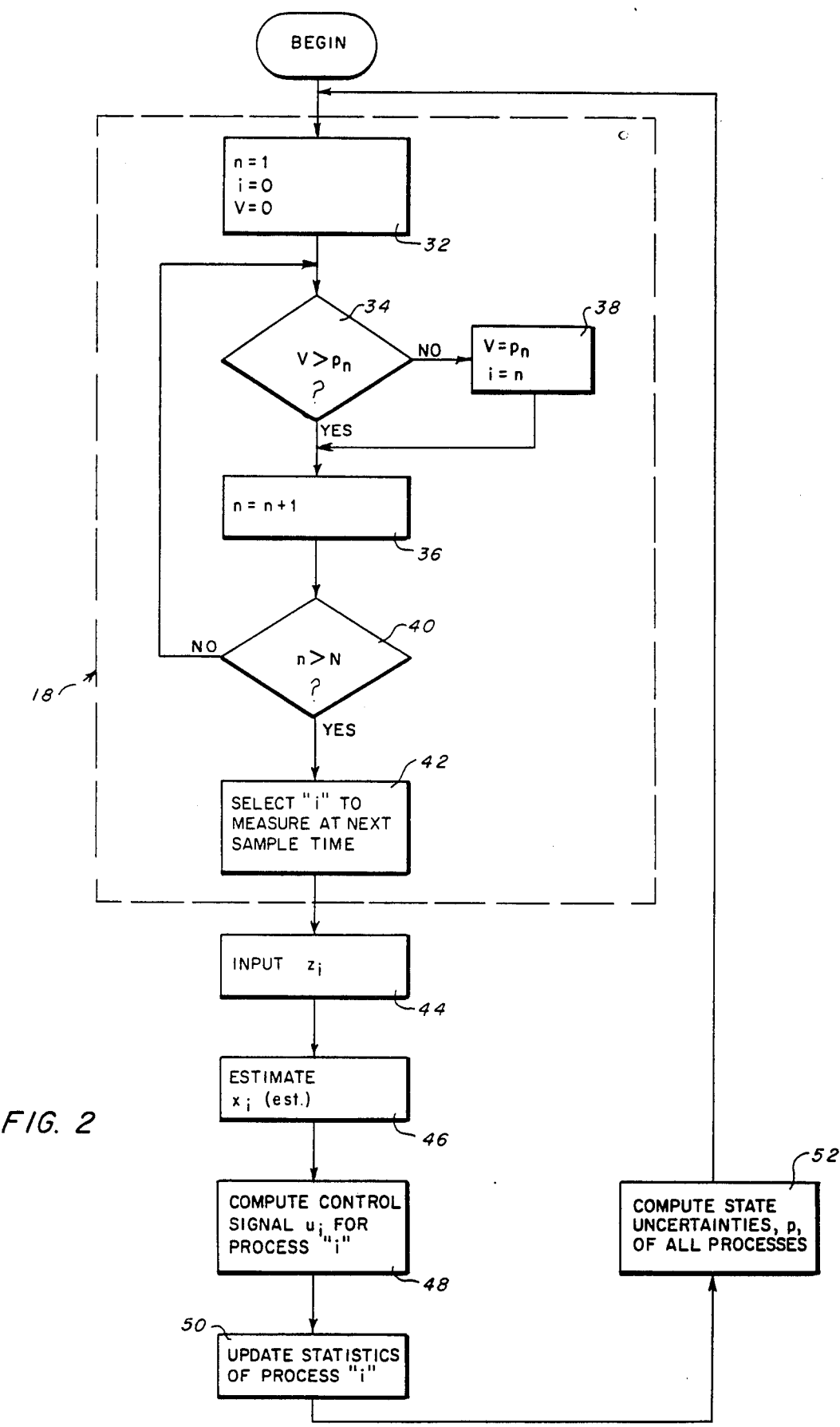
FIG. 2 is a specific pictorial flowchart illustrating the operation of the adaptive control apparatus of FIG. 1.
Figure 3:
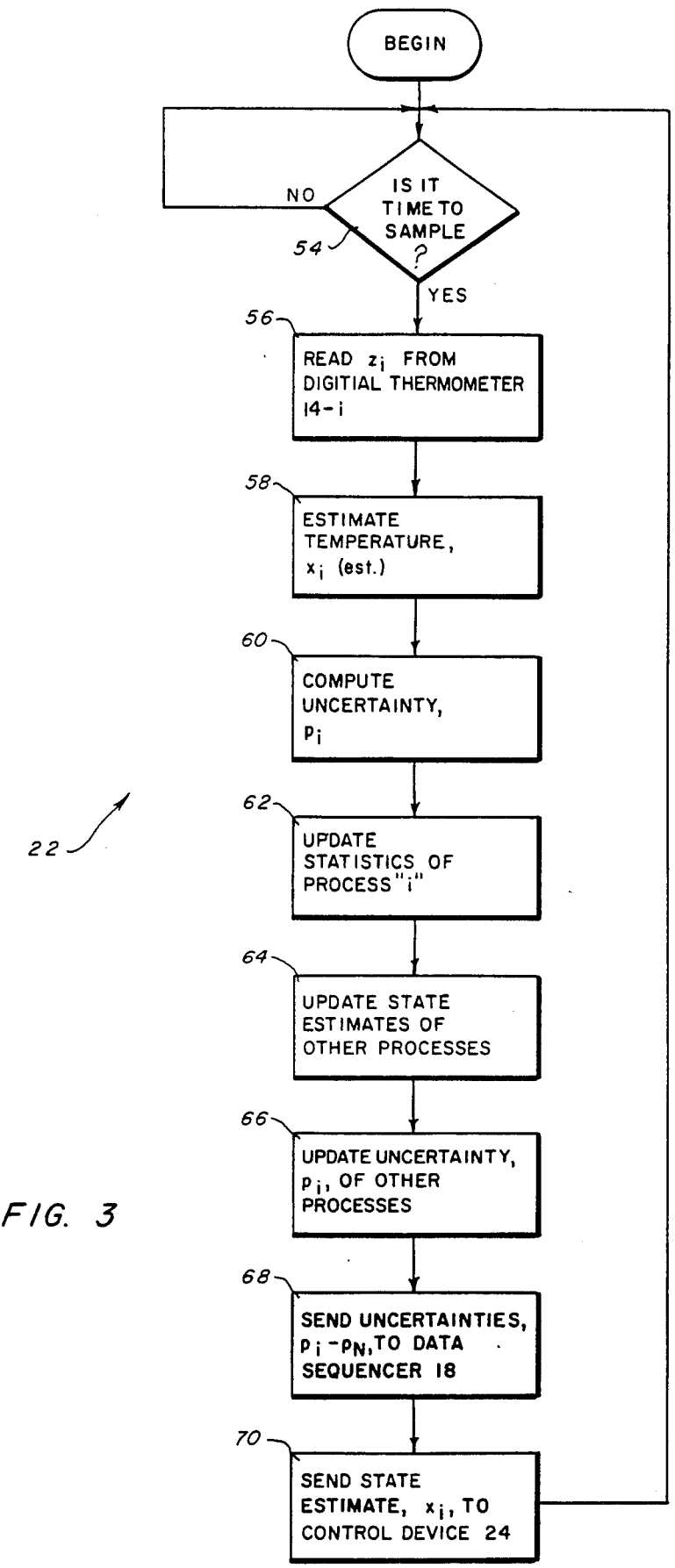
FIG. 3 is a specific pictorial flow chart giving more specific information concerning the processes and decisions related to the operation of the data sequencer and the temperature estimator of FIG. 1.

Details of the operation, according to a preferred embodiment of the present invention, are explained in conjunction with the FIGS. 1, 2 and 3.

Referring then to FIGS. 1 and 2 as viewed concurrently, in order to control the desired processes 12-1 through 12-N, initially, the temperature estimator 22 has an estimate of the temperature of each process as well as an estimate of the uncertainty in each of these estimates. These uncertainties, the error covariance matrices, $p_1$–$p_N$, are passed to the data sequencer 18 which selects the number of the process (i) which has the largest uncertainty in the estimate of the temperature. This operation is depicted in process block 32 decision block 34, process block 36, process block 38, decision block 40 and process block 42 which are representative of the operation and function of the data sequencer 18. To continue, the aforementioned number of the process (i) is passed to the electronic data selector 20 which operates to pass the selected measurement, $z_i$, from the corresponding one of the digital thermometers (14-i) through to the temperature estimator 22. The foregoing operation is illustrated in the process block 46, the process block 48, the process block 50 and the process block 52. As shown in the process block 52, after computation of the state uncertainties, p, of all of the processes 12-1, 12-2 through 12-N the process repeats itself.

FIG. 3 illustrates in a flowchart format the operation of the temperature estimator 22 of the adaptive control apparatus 10 of FIG. 1. Referring then to FIG. 1 and 2 as viewed concurrently, the decision block 54 waits until the next appropriate sample time and then continues to process block 56 which reads the digital thermometer (14-i). Next, the temperature $x_i$ is estimated as depicted by the process block 58 and the uncertainty in this estimation, $p_i$, is computed in process block 60. The statistics of the process noise are then updated for use during the next estimate computation in process block 62. The other state estimate uncertainties, p, are then updated in process blocks 64 through 66. Finally, the data is sent via process blocks 68 and 70 from the estimator 22 to the sequencer 18 and the control device 24. The control device 24 then takes the temperature estimate, $x_i$, and substracts it from the temperature reference input, x(ref), in the digital substractor 26. The result is then multiplied in digital multiplier 28 by a constant scale factor then passed to the electronic data distributer 30 where the control signal, $u_i$, is routed to the appropriate process $12_i$. The control signal, $u_i$, then actuates the corresponding heat/cooling device $16_i$. The process then repeats itself.

Accordingly, FIG. 1 illustrates a preferred implementation for an adaptive control apparatus configured for a centralize control of distributed processes. In general, these processes can be different with no loss of generality. Although this example is a scaler case with one variable (temperature) being controlled, the method is easily generalized to state variable concepts where the complete state vector of a system is controlled. In the example disclosed in FIG. 1, each of the processes controlled represents a room in a building which is subject to random, uncontrolled variables (process noise) such as varying amounts of sun, random numbers of people in the room, and various efficiencies of the heat/cool devices 16-1, 16-2 through 16-N. These continuely changing parameters can best be modeled as random noise and are treated as such in the realization of the Kalman filter in temperature estimater 22. Accordingly, the state vector consists of one variable, the room temperature.

To those skilled in the art, many modifications and variations of the present invention are possible in light of the above teachings. It is therefore to be understood that the present invention can be practiced otherwise then as specifically described herein and still be within the spirit and scope of the appended claims.

What is claimed is:

1. An apparatus for controlling multiple time-varying processes comprising:
   a plurality of processes 1 through N to be controlled and being configured so as to generate data $z_1$ through $z_N$ corresponding to each of said plurality of processes;
   an electronic data selector operatively connected to said plurality of processes and being configured to respond to a sequencer signal so as to route a selected one $z_i$ of the data $z_1$ through $z_N$ to the output thereof;
   first means operatively connected at its input to the output of said electronic data selector for estimating the values $x_1$ through $x_N$ of the data $z_1$ through $z_N$ of each one of said plurality of processes 1 through N as well as measuring of the uncertainties $p_1$ through $p_N$ in each of the estimates, said first means being configured to output at one output the uncertainties $p_1$ through $p_N$ and to output at another output the largest $x_i$(est) of the estimated values $x_1$ through $x_N$;
   a data sequencer operatively connected at its input to the one output of said first means and at its output to said electronic data selector, said data sequencer being configured to compare the uncertainties $p_1$ through $p_N$ for each estimate $x_1$ through $x_N$ so as to select the greatest uncertainty $p_i$, the greatest uncertainty $p_i$ then being used to generate the sequencer signal at the output of said data sequencer; and
   second means operatively connected to the another output of said first means, to said data sequencer and to said plurality of processes 1 through N to be controlled for controlling the appropriate one of said plurality of processes 1 through N as a function of the largest estimated value $x_i$(est) and a reference value x(ref) as controlled by said data sequencer.

2. The apparatus of claim 1 wherein each of said plurality of processes 1 through N are dissimilar.

3. The apparatus of claim 2 wherein each of said plurality of processes 1 through N are similar, and wherein each one thereof comprises:
   one of a plurality of digital thermometers 1 through N operatively connected to said electronic data selector for measuring the temperature and converting it to a digital word; and
   one of a plurality of heat/cool devices 1 through N operatively connected to the one of said plurality of digital thermometers 1 through N and to said second means for varying the temperature of the appropriate one of said plurality of processes 1 through N.

4. The apparatus of claim 3 wherein said second means comprises:
   a control device operatively connected at one input to the other output of said first means and at another input to a temperature reference x(ref) for computing a control signal $u_i$ at its output which is proportional to the difference therebetween; and
   an electronic data distributor operatively connected to the output of said control device, said data sequencer and to each one of said plurality of heat/cool devices 1 through N for distributing the control signal $u_i$ to the appropriate one thereof.

5. The apparatus of claim 4 wherein said control device comprises:
   a digital substractor for computing the error between the temperature x(ref) and the estimate $x_i$(est); and
   a digital multiplier for multiplying the output of said digital substractor by a predetermined fixed constant to scale the control signal $u_i$ at its output to the proper value.

* * * * *